United States Patent [19]

Hodes et al.

[11] Patent Number: 5,097,024
[45] Date of Patent: Mar. 17, 1992

[54] DNA PROBES FOR FINGERPINT ANALYSIS WITHOUT TANDEM REPEATS

[76] Inventors: Marion E. Hodes, 640 Edgemere Dr., Indianapolis, Ind. 46260; Franklin H. Norris, 5518 S. Arlington Ave., Indianapolis, Ind. 46237; Marquis Z. Hodes, 5588 W. 34th St., Indianapolis, Ind. 46224

[21] Appl. No.: 411,823

[22] Filed: Sep. 25, 1989

[51] Int. Cl.$^5$ .................. C12Q 1/68; C07H 21/04
[52] U.S. Cl. ............................ 536/27; 435/6
[58] Field of Search .................... 536/27; 435/6

[56] References Cited

FOREIGN PATENT DOCUMENTS 0264305 4/1988 European Pat. Off.
2166445 10/1985 United Kingdom.
8602948 5/1986 World Int. Prop. O.

OTHER PUBLICATIONS

Lebovitz (1989) Embo J., vol. 8, pp. 193–202.
Vassart et al., (1987), Science, vol. 235, pp. 683–684.
Tam et al. (1988), Biochem. Biophys. Acta, vol. 153, pp. 209–216.
Botstein et al., Am. J. Human Genet., 32:314–331 (1980).
Vassart et al., Science, 235:683–684 (1987).
Ishizaki et al., Biochem. Biophys. Res. Comm. 162(3):1030–1036 (1989).
Dijkema et al., Gene 18:143–156 (1982).
Runswick et al., Biochemistry, 28:9452–9459 (1989).

*Primary Examiner*—Johnnie R. Brown
*Assistant Examiner*—Gary L. Kunz
*Attorney, Agent, or Firm*—William B. Scanlon; Leroy Whitaker

[57] ABSTRACT

DNA probes for DNA fingerprint analysis. The DNA probes are 15 nucleotide sequences wherein 8 nucleotides of each sequence are G, 3 are T, 1 is C, 1 is A and 2 are A, C, G or T (N), except that the nucleotide sequence is not the M13 consensus sequence GAGGGTGGNGGNTCT. In particular, the 15-nucleotide sequence GGTGGNGATGGCTNG or as randomized variant of this sequence which is not the M13 consensus sequence, may be used as probes to detect hypervariable regions in genomic DNA. Methods for the preparation of such probes and for the detection of restriction length fragment polymorphisms using such probes are disclosed. The DNA probes are useful in genetic origin determination of human, animal or plant DNA-containing samples.

3 Claims, 2 Drawing Sheets

DNA PROBES FOR FINGERPINT ANALYSIS WITHOUT TANDEM REPEATS

BACKGROUND AND SUMMARY OF THE INVENTION

The present invention relates to the preparation of novel DNA probes. Each probe is a synthetic 15 nucleotide sequence comprising 8 G's, 3 T's, 1 C, 1 A and 2 N's (where N is A, C, G or T). The DNA probes thus may comprise a 15 nucleotide sequence that is GGTGGNGATGGCTNG or a randomized variant of that sequence, for example CTGGTGTGGAG-GAGG, excluding the M13 consensus sequence GAGGGTGGNGGNTCT, where N is A, C, G or T. The DNA probes are useful in probing human, animal or plant genomes. The invention further relates to an improved method of identifying genomic DNA using such probes, in particular by detecting polymorphisms. The DNA probes of the present invention are useful in many different areas, including the following:

1. paternity and maternity testing;
2. zygosity testing in twins;
3. cell chimerism studies, e.g., detection of donor versus recipient cells after bone marrow transplantation;
4. forensic medicine, e.g., identification of human remains, fingerprinting semen samples from rape victims or blood or hair samples from victim's clothing;
5. family group verification, e.g., in immigration or inheritance disputes;
6. tests for inbreeding;
7. general pedigree analysis;
8. identification of loci of genetic disease, to enable the construction of specific probes to detect a genetic defect;
9. animal or plant breeding and pedigree analysis authentication, e.g., routine control and checking of pure strains, checking pedigrees for litigation, providing genetic markers for economically important traits, checking for genetic relationships in order to prevent inbreeding of strains maintained in zoos;
10. quality control of cell lines, e.g.. checking for contamination and for routine identification; and
11. analysis of tumor cells for molecular genetic abnormalities.

Two principal methods of identifying genetic variation in genomic DNA are currently available: (1) detection of restriction fragment length polymorphisms (RFLPs), and (2) detection of hypervariable regions (HVRs) of DNA. RFLPs generally result from small-scale changes in DNA, usually base substitutions or microdeletion/insertion, which create or destroy specific restriction endonuclease cleavage sites. Many examples of RFLPs detected by human gene probes or random cloned DNA segments have been reported. (See Cooper and Schmidtke, 1984, Hum. Genet. 66:1–16).

Since the overall variability in human DNA is low with a mean heterozygosity per base pair of ~0.001–0.002 (Jeffreys et al., 1987, Biochem. Soc. Symp. 53:165-180; UK Patent Application GB 2166445A published May 8, 1986), restriction endonucleases will seldom detect a RFLP at a given locus. Variable sites are not uniformly dispersed; some regions (e.g. HLA gene cluster) are rich in RFLPs, whereas other genes (e.g. thyroglobulin) are markedly deficient in DNA variants. Even when detected, RFLPs are generally dimorphic (i.e., presence or absence of a restriction endonuclease cleavage site) and their usefulness as genetic markers is limited by their low heterozygosity. For a given diallelic marker, the maximum frequency of heterozygotes obtainable in a population in the absence of selection is 50%. (Jeffreys et al., 1987, supra). Thus, in pedigree analysis, all such RFLPs will be uninformative whenever critical individuals are homozygous.

Despite these limitations, RFLPs have provided numerous human genetic markers, which are useful in mapping human chromosomes. (Botstein et al., 1980, Am J. Hum. Genet. 32: 314-331). Most recently, RFLPs have also been used to detect markers linked to disease loci when the gene product of the locus is unknown (e.g., markers linked to Huntington's disease (Gusella et al., 1983, Nature 306:234-238), adult polycystic disease of the kidney (Reeders et al., 1985, Nature 317:542-544), and cystic fibrosis (Tsui et al., 1985, Science 230:1054-1057). Despite this progress, the logistics of detecting linkage with randomly selected markers are formidable. Since the human genome is ~3300 map units (cM) long, at least 115 uniformly spaced markers would have to be screened before there would be even a 50/50 chance that one marker would be linked within 10 cM of a defined disease locus. (Jeffreys et al., 1987, supra). Because most RFLPs are diallelic and would be uninformative in most pedigrees, the prior odds of detecting linkage between a disease locus and a random marker in a given pedigree are even lower. This second problem might be circumvented by using more highly polymorphic markers.

Recently, localized regions of high variability termed hypervariable regions (HVRs) have been identified in and isolated from human DNA. The availability of probes for such HVRs that show multiallelic variation and correspondingly high heterozygosities would simplify and be useful for genetic analysis. The chance discovery by Wyman and White, 1980, Proc. Natl. Acad. Sci. USA 77:6754-6758, of a random human DNA segment which defined a multiallelic locus was the first direct demonstration that HVRs exist in human DNA. Recently this variable DNA region itself has been cloned (Wyman et al., 1985. Proc. Natl. Acad. Sci. USA 82:2880-2884). Since the initial discovery by Wyman and White, 1980, supra a number of other HVRs have been discovered by chance in human DNA, including: (1) a region 5' to the human insulin gene (Bell et al., 1982, Nature 295:31-35); (2) a region 3' to the c-Ha-rasl oncogene (Capon et al., 1983, Nature 302:33-37); (3) at least 3 HVRs in and around the α-globin gene cluster (Higgs et al., 1981 Nucleic Acids Res. 9:4213-4224; Proudfoot et al., 1982, Cell 31:553-563; Goodbourn et al., 1983, Proc. Natl. Acad. Sci. 80:5022-5026; Jarman et al., 1986, EMBO J. 5:1857-1863); and (4) a region in the collagen type II gene (Stoker et al., 1985, Nucleic Acids Res. 13:4613). In each example listed above, the HVR consists of tandem repeats of a short sequence (a "minisatellite"). More recently, other minisatellite elements have been discovered in the human factor VII gene (Murray et al., Nucleic Acids Res. 16:4166), 3' to the human apolipoprotein B-100 (Apo B) gene (Huang et al., 1987, J. Biol. Chem. 262:8952-55), in the human apolipoprotein C-II (Apo C-II) gene (Das et al., 1987, J. Biol. Chem.

262:4787-93), and in two loci from the pseudoautosomal region of the human X and Y chromosomes (Simmler et al., 1987, EMBO J. 6:963-69).

According to Jeffreys al., 1987, supra, the hypervariability at minisatellites results from changes in the number of repeats, presumably driven either by unequal recombination between misaligned minisatellites or by slippage at replication forks leading to the gain or loss of repeat units. The resulting length variability may be high. In some cases, a multiplicity of different length alleles may be observed, and the frequency of heterozygotes may approach 100% provided that the restriction enzyme does not cleave the minisatellite unit itself. Detection of the minisatellite length variation (i.e. RFLPs at these HVRs) is independent of the restriction enzyme used, and these loci, therefore, provide ideal markers for human genetics. (Reeders et al., 1985, Nature 317:542-544). Nakamura et al., 1987, Science 235:1616-22 have used the term variable number of tandem repeats (VNTR) locus to designate a single locus which comprises a genetic sequence that contains tandem repeats of that sequence. Thus, the terms HVRs, minisatellites and VNTRs may be used interchangeably to indicate polymorphic regions of DNA in which the polymorphisms are due to variation in the number of tandem repeats of a short DNA sequence.

The total number of hypervariable loci in human DNA is not known, but appears to be large. From a screening of 1680 different recombinants from a human genomic library (Knowlton et al., 1986, Blood 68:378-385), at least 12 clones contained highly polymorphic regions. This would suggest that the human genome could contain $\geq 1500$ HVRs. These HVRs may provide highly informative markers for the human linkage map, if they can be isolated.

Weller et al., 1984, EMBO J. 3:439-446, have described a small minisatellite comprised of four repeats of a 33 bp sequence found within one of the introns of a human myoglobin gene. A DNA probe comprising tandem repeats of this 33 bp sequence from the myoglobin gene was used to probe the human genome. Polymorphic variation was observed at several different regions in the genomic DNA of 3 related individuals (mother, father, daughter). The length variation was observed in fragments 2-6 kb in size, and was thought to be due to length variation of more than one minisatellite region.

More recently, Jeffreys has described a region of DNA, termed a common core region, which has a high degree of homology with several minisatellites. In PCT Application WO 86/02948 (published May 22, 1986) and European Patent Application 0238329A2 (published Sept. 23, 1987), Jeffreys has disclosed and claimed a DNA probe (and methods of preparing such a probe) which has as its essential constituent this short core sequence (approximately 16 nucleotides) tandemly repeated at least 3 times. According to Jeffreys, a probe having a tandem repeat of such a core sequence is able to detect many different minisatellite regions in genomic DNA. Because the probe detects many minisatellite regions, a fingerprint is obtained which is in essence unique for an individual. Further, according to Jeffreys, previously known probes were only capable of detecting a single minisatellite region and thus incapable of such individual fingerprinting. In particular, the probes disclosed and claimed by Jeffreys contain tandem repeats (at least 3 repeats are required) of a "core" sequence of 6 to 16 nucleotides having a high degree of homology with a nucleotide sequence of the general structure 5'- H.(J.core.K)$_n$.L-3', where n is at least 3 and the core includes any of the following:

| | |
|---|---|
| GGAGGTGGGCAGGAXG | (2) |
| AGAGGTGGGCAGGTGG | (3) |
| GGAGGYGGGCAGGAGG | (4) |
| T(C)$_m$GGAGGAXGG(G)pC | (5A) |
| T(C)$_m$GGAGGA(A)$_Q$GGGC | (5B) | where
X=A or G; Y=C or T; m=0, 1 or 2;
p=0 or 1; Q=0 or 1.

In order to produce "an operable probe," Jeffreys states that the core sequence in itself is insufficient. What is required is to produce a polynucleotide containing tandem repeats (at least 3) of the core sequence or derivatives thereof. Jeffreys' probes are thus segments of minisatellite DNA and may be isolated as minisatellite fragments from human genomic DNA and cloned or may be synthetically prepared minisatellite sequences. Jeffreys, supra, has used these probes for twin zygosity studies. In addition, Min et al., 1988, British J. Haematol. 68:195-201, recently described the use of some of the minisatellite DNA probes described and claimed by Jeffreys in PCT Application 0238329, supra to identify cell origin after bone marrow transplantation.

Most recently, Vassart et al., Science 235:683-684 (1987) and European Patent Application 0264305 (published Apr. 20, 1988) have described a DNA probe derived from a sequence from wild-type M13 bacteriophage that identifies hypervariable minisatellite regions present in the human genome, provided that no competitor DNA is used during hybridization. Fish DNA (e.g. salmon sperm or herring) which is typically used during hybridizations will block or compete with the hybridization of the M13 DNA.

The effective sequence in M13 was identified as two clusters of 15 bp tandem repeats within the protein III gene of M13. The probe disclosed and claimed by Vassart et al., has the following M13 consensus sequence:

(GAGGGTGGNGGNTCT)$_n$ or
(Glu-Gly-Gly-Gly-Ser)$_n$

One of the repeat clusters was isolated as an ~280 bp HaeIII-ClaI fragment and was used as a probe on Southern blots of HaeIII-digested human or animal DNA. Vassart et al., 1987, supra, showed that the pattern obtained with the ~280 bp M13 probe was clearly different from that obtained with Jeffreys' minisatellite DNA probe. Westneat et al., 1988, Nucleic Acids Res. 16: 4161, have recently described improved hybridization conditions for the Vassart et al., supra M13 probe and the Jeffreys, supra, minisatellite probes, to eliminate inconsistent hybridization and often high levels of background hybridization.

In addition to cloned DNA probes such as those described by Jeffreys, supra or Vassart et al., supra, oligonucleotide probes have also been used to detect HVRs or VNTR loci. Oligonucleotide probes have several advantages over cloned minisatellite probes since they may be readily synthesized and reduce hybridization and exposure times. However, it is difficult to discover what sequences will function as probes to detect HVR. For example, Schafer et al., 1988, Nucleic Acids Res. 16:5196 investigated the use of 8 different simple repetitive oligonucleotides to screen human DNA. Six of the 8 synthetic oligonucleotides tested were ineffective as probes. The two probes that were effective were the repetitive synthetic oligonucleotides (CAC)$_5$ and (GACA)$_4$. The (GACA)$_4$ probe reported previously by Ali et al., 1986, Hum. Genet. 74:239–43 was less polymorphic than the (CAC)$_5$ probe but was one order of magnitude more sensitive than the (CAC)$_5$ probe.

In contrast to the simple repetitive oligonucleotides used by Schafer et al., 1988, supra and Ali et al., 1986, supra, several groups have started with known sequences of HVRs to prepare synthetic oligonucleotide probes corresponding to these known sequences. For example, in Nakamura et al., 1987, supra. 16–20 oligonucleotide probes were synthesized based on the previously reported sequences of HVRs from myoglobin (Jeffreys et al., 1 1985, Nature 314:67–73) zeta-globin (Proudfoot et al., 1982, Cell 31:553) insulin (Bell et al., 1982, Nature 295:31–35) and the X-gene region of HBV. The probes contained a somewhat variable core sequence GGGGTGGGG and the almost invariant sequence GTGGG.

In subsequent studies, Nakamura et al., 1988, Am J. Hum. Genet. 43:854–59 prepared pools of synthetic 18-base oligonucleotides based on the previously reported sequences from the zeta-globin (Proudfoot et al., 1982, supra), insulin (Bell et al., 1982, supra), myoglobin (Jeffreys et al., 1985, supra), Harvey-ras (Capon et al., 1983, Nature 302:33–37) genes and other loci known to contain HVRs (Nakamura et al., 1987, supra). All 18-base oligonucleotides included GNNGTGGG as a core sequence and the 12 bases outside this core sequence were chosen randomly. In particular, each oligonucleotide used as a probe was actually a pool of 256–1,024 different sequences, because each included 4 or 5 N's (where N is A, G, C or T). In both Nakamura et al., 1987, supra, and Nakamura et al., 1988, supra, the probes were used to screen human genomic libraries for the purpose of identifying locus-specific DNA markers for human gene linkage studies.

The present invention relates to novel DNA probes derived from the M13 consensus sequence, which are randomized variants of the M13 sequence. It has now been unexpectedly found that a 15-nucleotide sequence GGTGGNGATGGCTNG or a randomized variant of this sequence which is not the M13 consensus sequence, detects HVRs in genomic DNA and with such precision as to enable individuals to be identified or fingerprinted by reference to variations in their DNA in these regions. A variety of different restriction endonucleases (including HaeIII, AluI, HinfI, MboI, or SauC13AI) may be used to digest the DNA that is to react with the DNA probes of the present invention. Such an excellent result is highly unexpected, since there was no suggestion that a sequence other than the precise M13 consensus sequence itself tandemly repeated as defined by Vassart et al., supra would be capable of detecting HVRs. In particular, it is impossible to predict whether such a randomized sequence would function as a probe better, worse, the same or not at all as compared with the M13 consensus sequence. The discovery of such randomized non-repetitive sequences and demonstration of such unexpected and excellent results using such sequences lends an unusual degree of unobviousness to the inventive art.

The prototype sequence GGTGGNGATGGCTNG [or Gly-Gly-Asp-Gly-Trp] of the present invention is a significantly different and unique sequence as compared with the prior art M13 consensus sequence. For example, a search analysis of gene and DNA sequences contained in the computer database of genetic sequences known as GenBank, revealed that 1120 matches and 934 loci (loci may contain more than one match) contained the M13 consensus sequence, whereas 1378 matches and 1171 loci contained the prototype sequence. These numbers were obtained from a search of GenBank 60.0 (6/89) allowing 2 base mismatches, with all parameters identical for the M13 sequence and the prototype sequence. When the loci containing the M13 sequence or the prototype sequence of the present invention were further analyzed, only 150 loci were found in common between the M13 and prototype sequences. Surprisingly, there were 784 M13-unique loci and 1021 prototype-unique loci. Similar results may be obtained by searching a GenBank version other than GenBank 60.0 (6/89). The discovery that 1021 gene loci contain only he prototype sequence while 784 different gene loci contain only the M13 sequence suggests that a novel probe of the present invention which comprises the prototype sequence is significantly different from the prior art M13 sequence. These differences have been confirmed in comparative hybridization studies with an M13 probe. The restriction fragment patterns obtained with probes of the present invention are significantly different from patterns obtained with an M13 probe.

A probe according to the present invention is unusually effective as a probe for DNA fingerprinting, and gives clean, clear fingerprints when one of any number of restriction endonucleases is used to digest the DNA sample to be probed. It is also unusually effective in light of the present discovery that the 15-nucleotide sequence alone, and not a tandem repeat of that sequence, is effective as a probe of HVRs in genomic DNA. This is particularly unexpected in light of PCT Application 0238329 (PCT/GB85/00477) which teaches that the mere recognition or identification of a particular 16-nucleotide core sequence is insufficient in itself for the production of an operable probe to detect HVRs; an operable probe requires a polynucleotide containing tandem repeats of the core sequence or a derivative of the core sequence. Similarly, European Patent Application 0264305A2 describes a probe comprising an ~280 bp HaeIII-ClaI fragment from M13 which contains multiple tandem repeats of the preferred M13 consensus core sequence. It is also unusually effective in that a 15-nucleotide sequence which itself contains no simple repetitive units, is effective as a probe of HVRs in genomic DNA. This is particularly unexpected in light of prior art probes (CAC)$_5$ and (GACA)$_4$ comprising simple repetitive sequences as described by Shafer et al., 1988, supra and Ali et al., 1986, supra.

In a particularly preferred embodiment of the present invention, the DNA probe is a 15-nucleotide sequence that is GGTGGAGATGGCTGG. This sequence was itself randomized 35 times, producing 35 related sequences with identical base content but permuted sequences. Thus, a DNA probe according to the present invention is a simple and extremely sensitive detector of DNA polymorphisms, that works by detecting RFLPs of HVRs. In contrast to the probes of Jeffreys, supra, and Vassart et al., supra, it is effective as a 15-nucleotide (15-mer) and does not require a tandem repeat of the 15-mer to be operative as a probe that detects DNA polymorphisms.

For purposes of the present invention as disclosed and claimed herein, the following terms are defined below:

Base pair (bp) or Nucleotide (nt) - used synonymously. Both can refer to DNA or RNA. The abbreviations A,C,G,T or U refer conventionally to the nucleotides (deoxy)adenosine, (deoxy)cytidine, (deoxy)guanosine, and thymidine or uridine monophosphates. In double-stranded DNA, base pair may refer to a partnership of A with T or C with G.

Consensus core sequence a sequence which can be identified as the closest match among a number of repeat sequences (e.g. among the repeat units of two or more different minisatellites).

Hypervariable Regions (HVRs) - a region of human animal or plant DNA at a recognized locus or site which occurs in many different forms, for example, as to length or sequence.

Minisatellite - a variable region of human, animal or plant DNA which is comprised of tandem repeats of a short DNA sequence, in which all repeats may not necessarily show perfect identity of sequence and in which the number of repeats may vary among different individuals.

M13 consensus sequence a sequence tandemly repeated in M13 genomic DNA that is GAGGGTGGNGGNTCT, where N is A, C, G, or T.

% Similarity - in comparing two sequences A and B (e.g. two tandem repeats or repeat sequences), the percentage similarity is given by the number of base pairs in A, less the number of base pair substitutions, additions or deletions in B, which would be necessary in order to give the sequence of A, expressed as a percentage. For example, the % similarity between two sequences ATGC and AGC is 75% (4−1=3 and ¾=75%).

Polymorphic/Polymorphisms - a gene or other segment of DNA which shows variability from individual to individual or between a given individual's paired chromosomes (e.g., a heterozygous individual).

Restriction Fragment - any linear DNA molecule generated by the action of one or more restriction enzymes.

Restriction Fragment Length Polymorphism(s) (RFLPs)-a polymorphism revealed by digestion of DNA with a restriction enzyme.

Tandem Repeat or Repeat Sequence - a polynucleotide sequence which is perfectly or imperfectly repeated in series.

BRIEF DESCRIPTION OF THE FIGURES

FIG. 2 shows DNA fingerprints of various recipients of bone marrow transplants (pre- and post-transplant). along with the DNA fingerprints of the bone marrow donors: Lanes 3, 4 and 5 are the pre-transplant (88-BM-0003), donor (88- BM-0004), and post-transplant (88-BM-0012) patterns, respectively; lanes 6, 7 and 8 are donor (87-BM-0017), pre-transplant recipient (87-BM-0019) and post-transplant recipient (88-BM-0013) patterns, respectively; lanes 9, 10 and 11 are pre-transplant recipient (87-BM-0006), donor (87-BM-0008) and post-transplant recipient (87-BM-0016) patterns, respectively; and lanes 12, 13 and 14 are donor (87-BM-0004-A), pre-transplant recipient (87-BM-0005-A) and post-transplant recipient (87-BM-0024) patterns, respectively. Lane 1 is a standard marker DNA (λ-HindIII) and lane 2 is a control genomic DNA (417-E).

DETAILED DESCRIPTION

The present invention relates to novel DNA probes which comprise a 15-nucleotide sequence that contains 8 G nucleotides, 3 T nucleotides, 1 C nucleotide, 1 A nucleotide and 2 nucleotides (N) which may be A, C, G or T, which is not the M13 consensus sequence GAGGGTGGNGGNTCT (where N is A, C, G or T). A preferred embodiment is a DNA probe comprising a 15-nucleotide sequence that is GGTGGNGATGGCTNG, where N is A, C, G or T. Other embodiments comprise random variants of this sequence. A particularly preferred embodiment is a DNA probe comprising a 15-nucleotide sequence that is GGTGGAGATGGCTGG. The invention further relates to improved methods of preparing DNA probes useful in the detection of restriction fragment length polymorphisms of hypervariable regions of DNA (RFLPs of HVRs) and thus useful in determining the genetic origin of human, animal or plant DNA.

Single-stranded DNA oligonucleotide fragments used in the construction of a DNA probe according to the present invention were chemically synthesized in a DNA synthesizer (Example 2). Many DNA synthesizing instruments are known in the art and can be used to synthesize single-stranded oligonucleotide fragments. A particularly preferred embodiment of the present invention has the following structure: 5'-GGTGGAGATGGCTGG -3'. Each oligonucleotide fragment synthesized and useful as a probe according to the present invention comprises at least one strand that is a 15-nucleotide sequence, and which contains 8 G's, 3 T's, 1 C, 1 A and 2 N's where N is A, C, G or T, but is not the M13 consensus sequence. The M13 consensus sequence described by Vassart et al., supra, (GAGGGTGGNGGNTCT or Glu-Gly-Gly-Gly-Ser) is contained in two clusters of 15 bp tandem repeats within the protein III gene of M13. One of these repeat clusters (∼280 bp) was isolated as an ∼280 bp HaeIII-ClaI fragment and used as a probe. In contrast, the DNA probes of the present invention comprise unique sequences that are significantly different from the M13 consensus sequence. In addition, the synthetic sequences of the present invention are not tandemly repeated in order to produce an operable DNA probe.

The DNA probes of the invention may be labeled and used in hybridization experiments to detect DNA polymorphisms, thus making the probes useful in establishing the identity of human, animal or plant DNA. The probes have proven particularly useful in the determination of twin zygosity at birth (Example 4). Determination of zygosity of twins is of importance not only for epidemiological, genetic and obstetric studies, but because of the difference in prognosis between monozygotic and dizygotic twins. Monozygotic or identical twins generally have lower birth weights, more medical complications and higher mortality rates than dizygotic twins. Newborn twins of unlike sex are always dizygotic. Newborn twins of the same sex may be monozygotic or dizygotic. In particular, if the placental membrane can be examined and is found to be monochorionic, then the twins are monozygotic. In cases of a dichorionic placental membrane (or cases in which the membrane is not examined) a variety of methods have been employed to determine zygosity, including assessment of general appearance, fingerprinting, skin grafting, taste testing and determination of genetic markers. (Lykken, D. T., 1978, Behavioral Genetics 8: 437-473). Only the last method (determination of genetic markers) is highly accurate, however, large numbers of such markers must usually be investigated because of relatively low mean heterozygosities of most protein and antigen variants.

Figure 1:
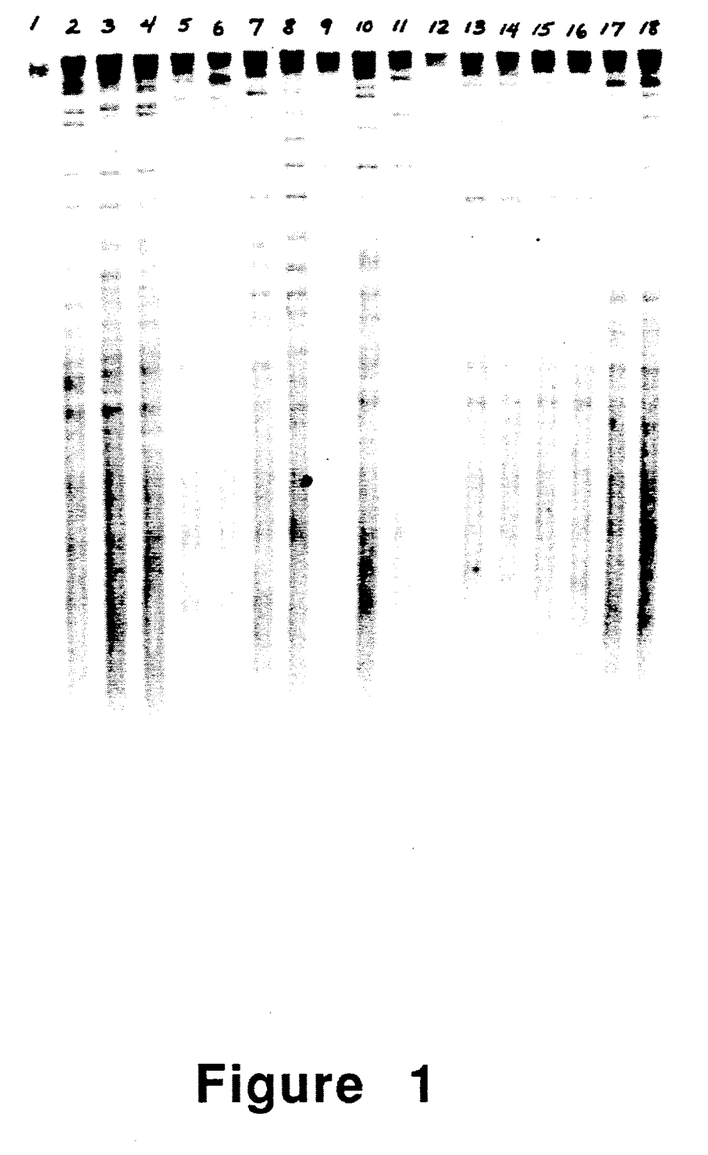
FIG. 1 shows DNA fingerprints of various twins listed in Table I: lanes 3 and 4, VA-5027 and VA-5028 (case 0004); lanes 5 and 6, VA-5053 and VA-5054 (case 0006); lanes 7 and 8, VA-5185 and VA-5186 (case 0014); lanes 9 and 10, VA-4149 and VA-4150 (case 0001); lanes 11 and 12, VA-5001 and VA-5002 (case 0002); lanes 13 and 14, VA-5015 and VA-5016 (case 0003). Lane 1 is a standard marker DNA (λ-HindIII) and lane 2 is a control genomic DNA (417-E).

Table I in Example 4 is a summary of the results of DNA analysis from 52 sets of twins with the DNA probes of the present invention. The resulting individual-specific DNA "fingerprints" obtained demonstrate such variability that only monozygous twins show identical patterns as shown in FIG. 1. In 21 of the 52 cases summarized in Table I where zygosity could be determined from sex observation or placental examination, the results of DNA analysis using a DNA probe of the present invention agreed with these findings. Methods using such a probe in accordance with the present invention allows rapid determination of zygosity. DNA probes of the present invention therefore provide an improved single genetic test that should permit the positive determination of zygosity in all cases of multiple pregnancy.

The DNA probes of the present invention have also proven particularly useful in the identification of the donor or recipient origin of hematopoietic cells after allogeneic bone marrow transplantation (Example 5). This identification is valuable for assessing the speed of engraftment, for detecting any residual population or subpopulation of normal recipient cells, and for recognizing relapse at an early stage. When the bone marrow donor and recipient are of opposite sex, analysis of sex chromosomes in dividing cells may provide the necessary information. Such cytogenetic methods are thus limited in their usefulness to such cases. A further limitation of such methods is that they selectively examine cells capable of undergoing mitosis in vitro and are based on the existence of a specific cytogenetic difference between donor and recipient, such as a sex chromosome.

When dividing cells are not available for analysis or when donor and recipient are of the same sex, other methods must be used. A variety of methods have been employed to characterize the donor or recipient origin of cells in the bone marrow and peripheral blood of a patient after a bone marrow transplant. These methods include erythrocyte antigen typing, HLA-typing, immunoglobulin isotyping, determination of leucocyte isozymes or genetic polymorphisms in DNA (see, for example, Ginsberg et al., 1985, J. Clin. Invest. 75:596-603; Blazar et al., 1985, Blood 66:1436-1444; Minden et al., 1985, J. Clin. Invest. 75:91-93; Knowlton et al., 1986, Blood 68:378-385). While the last method (genetic polymorphisms in DNA) is useful in most cases (perhaps 95% of cases), it requires the use of a panel of up to 10 different probes recognizing polymorphic loci in the human genome. In contrast, the DNA probes of the present invention appear to detect large numbers of distinct polymorphic sites in the human genome and thus give rise to a series of restriction fragments of differing size for any one individual. The number and precise location of these fragments are so variable that each DNA pattern obtained may be considered to be a DNA "fingerprint", that is, having the same degree of individual specificity as do fingerprints. The DNA probes of the present invention thus may be especially useful in differentiating DNA from two closely-related individuals, as is the usual case in clinical bone marrow transplants.

Figure 2:
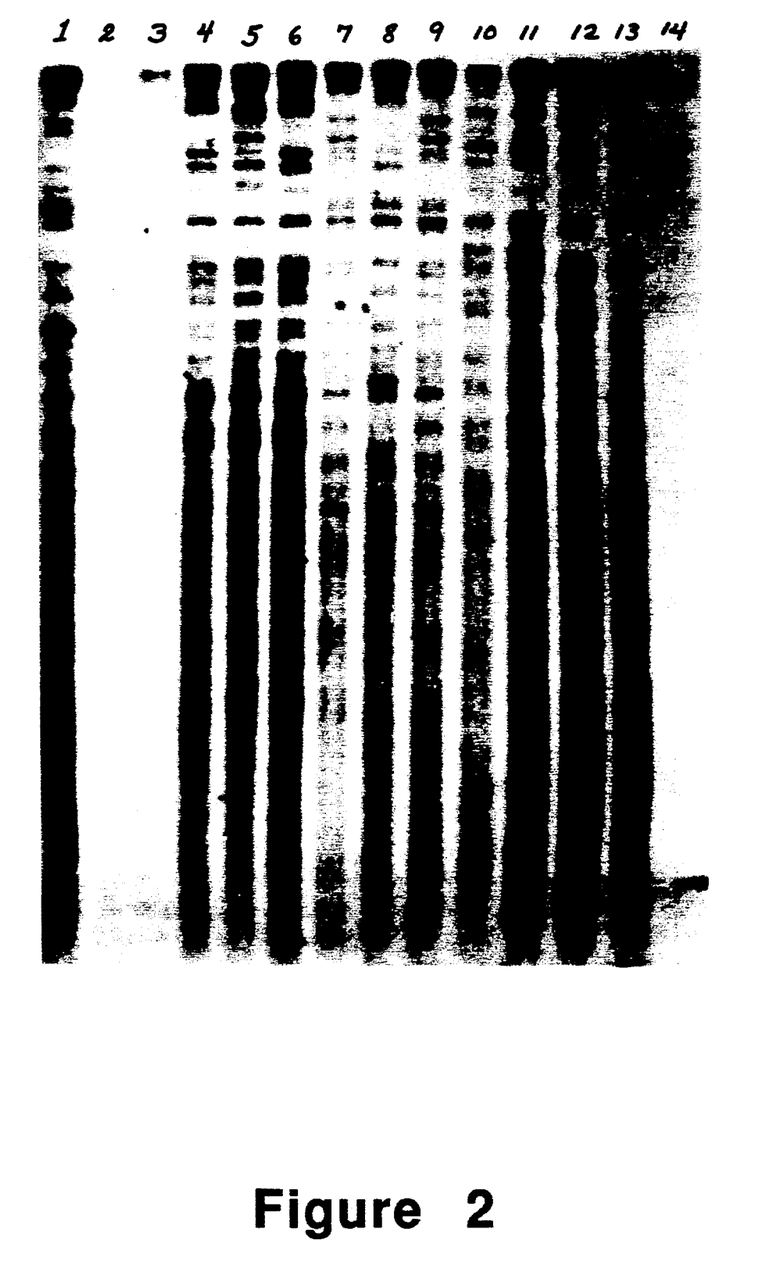

The DNA probes of the present invention were used, as described in Example 5, to analyze DNA from bone marrow transplant patients. Table II is a summary of the results of the DNA analysis of 46 different bone marrow samples. The resulting individual-specific DNA "fingerprints" obtained demonstrate such variability that donor- and recipient-cell DNA is easily distinguished (FIG. 2). In 30 cases, the pattern obtained was identical to the donor type, indicating a "take" of the bone marrow graft and a persistence of the "take". In 6 cases, the pattern obtained was a hybrid pattern of both donor and recipient types. This indicated chimerism. In 10 cases, the pattern obtained was identical to the recipient type, indicating a failure to engraft.

Thus, the DNA probes of the present invention may be useful in an improved method that permits rapid determination of cell origin after transplantation. These DNA probes are very sensitive detectors of RFLPs in HVRs of genomic DNA. Signals can be readily obtained from 0.2 $\mu$g or less of human genomic DNA. Furthermore, depending on the genotypes of the individuals tested, these DNA probes can detect an admixture of 5% or less of one individual's DNA with another.

The DNA probes of the present invention are also useful in forensic applications.

The following Examples more fully describe the DNA probes and methods of the present invention. General methods for the preparation and analysis of DNA may be found in various laboratory manuals, including *Current Protocols In Molecular Biology* (Ausubel et al., eds., 1989, Greene Publishing Associates and Wiley-Interscience). Those skilled in the art will recognize that the particular reagents, equipment, and procedures described in the Examples are merely illustrative and do not limit the present invention.

EXAMPLE 1

Randomization of M13 Consensus Sequence and GenBank Analysis

The M13 sequence was initially randomized manually by the method of random sampling without replacement to produce random sequences. Later, a computer program was written that implemented an algorithm that produces a random sequence by sampling without replacement. An English language version of the algorithm is given, below. The physical or computerized procedure can be repeated to produce over 9 million random sequences.

Several of the random sequences that were obtained were synthesized, labeled and used as DNA probes, in substantial accordance with the procedures of Example 2. When one such sequence GGTGGAGATGGCTGG was compared to a tandem alignment of the M13 sequence, at most nine bases were found to be identical.

```
      M13 Tandem    M13 Tandem
      §------1------  §------2------

M13:  GAGGGTGGNGGNTCTGAGGGTGGNGGNTCT
      | | | | :  |  :              |
Probe:     GGTGGAGATGGCTGG
```

Thus, the maximum similarity between the M13 sequence and the random probe is 9/15 or 60 percent. Since the N's, the undefined bases, in the M13 sequence are allowed to match any base in the synthesized probe, the percent similarity may be as low as ~47 percent. When the 15-nucleotide GGTGGAGATGGCTGG probe sequence is directly compared to the 15 nucleotide (non-tandem) M13 sequence, the maximum percent similarity is again 60 percent. Again, the percent similarity may be as low as ~47 percent.

Genetic Sequences Database (GenBank) is a computerized database of nucleotide and gene sequences which was maintained under an NIH contract until 1988 by BBN Laboratories, Inc. (10 Moulton Street, Cambridge, Mass. 02238) and thereafter by IntelliGenetics. GenBank may be searched using the software described by Devereux et al., 1984, Nucleic Acid Res. 12: 387-95. For example, when the GenBank DNA database (release 60, 6/89) was searched for the GGTGGAGATGGCTGG probe sequence allowing two mismatches, qualifying sequences in 178 entries were found. The matching entries included sequences from viruses, bacteria, insects, plants, and animals, representing structural genes, Alu sequences, oncogenes, and 5' and 3' flanking regions.

In an earlier analysis, the GenBank DNA database (Version 56, 11/86) was searched for the GGTGGAGATGGCTGG probe sequence allowing, 0, 1, 2 or 3 mismatches. There was one perfect match (i.e. 0 mismatches) occurring in the second open reading frame of the plasmid pWRCIT, which contains an E. coli citrate utilization determinant region. When a single-base mismatch was allowed, there were 13 matches. Most of these 13 matches were mouse sequences, but this may reflect bias in the distribution of reported sequences. Matches occurred in 117 sequences when two mismatches were allowed, and in 1367 when three mismatches were allowed. Data were accumulated for all three or fewer mismatches, and from the data a consensus sequence GGTGGNGATGGTNG was developed and, in particular, a preferred variant of this consensus sequence GGTGGAGATGGCTGG was developed.

The GGTGGAGATGGCTGG probe sequence was itself randomized 35 times, producing 35 related sequences with identical base content but permuted sequences. GenBank was searched with these sequences allowing three mismatches (Version 60.0, 6/89). These sequences are illustrated below, along with the number of GenBank sequences that matched each sequence:

|          | Sequence        | Matches in GenBank |
|----------|-----------------|--------------------|
| M13      | GAGGGTGGNGGNTCT | 817-1455           |
| Prototype| GGTGGAGATGGCTGG | 2052               |
| Random01 | AATGCGGTGGGGGGT | 741                |
| Random02 | ATCGTGGTGGAGGGG | 1335               |
| Random03 | ATTGGGCGGGGAGTG | 682                |
| Random04 | CAGTGGTGTGGAGGG | 1415               |
| Random05 | CGGAGGAGTTGTGGG | 1286               |
| Random06 | CGGGGGATGTTGGGA | 1063               |
| Random07 | CGGGGTGGGGTAATG | 773                |
| Random08 | CGGGGTGTGAGGTAG | 658                |
| Random09 | CGGTTGTGAGGGGGA | 706                |
| Random10 | CTGGTGTGGAGGAGG | 2360               |
| Random11 | GAATGGGGCGGTGTG | 763                |
| Random12 | GACGGTGGTGAGGTG | 1226               |
| Random13 | GAGTACGGTGGGGTG | 836                |
| Random14 | GAGTCGGTGGGTAGG | 687                |
| Random15 | GAGTGGGTTAGGGGC | 934                |
| Random16 | GGCGGGTGGTGGTAA | 1016               |
| Random17 | GGCGGTTTAGGAGGG | 783                |
| Random18 | GGCGTGAGGGAGGTT | 833                |
| Random19 | GGGCATAGGTTGGGG | 1043               |
| Random20 | GGGCTTTGAGGGGGA | 1449               |
| Random21 | GGGGCAGTAGTGGGT | 1228               |
| Random22 | GGGGGGAGTTGCAGT | 1195               |
| Random23 | GGGGGGTGCTGGAAT | 1199               |
| Random24 | GGGGTATGTGCGAGG | 582                |
| Random25 | GGTGGGCTTGAGGGA | 1419               |
| Random26 | GTAAGGGGGGCTTGG | 783                |
| Random27 | GTGAGGCGGGTGAGT | 945                |
| Random28 | GTGCAGGATGGTGGG | 1603               |
| Random29 | GTGGTATGGGAGCGG | 836                |
| Random30 | GTGTGGGTGGCAGAG | 2078               |
| Random31 | TAAGGTGGGGGCGGT | 870                |
| Random32 | TAGCGGATGGGGTGG | 998                |
| Random33 | TGAGAGTGGGGGGCT | 1321               |
| Random34 | TGGGAGTGCGAGGGT | 924                |
| Random35 | TGGGGGGAATTCGGG | 716                |

Two of the 35 randomized sequences had more matches than the GGTGGAGATGGCTGG probe sequence (2360 and 2078 vs. 2052). The M13 consensus sequence contains 2N's, which may be CC, CT, TC or TT, respectively. The GenBank search revealed 1100, 817, 1424 and 1455 matches, respectively. Twenty-four of the 35 randomized sequences had more matches than the GAGGGTGGCGGTTCT M13 sequence; 13 had more matches than the GAGGGTGGCGGCTCT M13 sequence; and 4 had more matches than the GAGGGTTGGTGGCTCT and GAGGGTGGTGGTTCT M13 sequences. While a high number of matches of the randomized sequence in GenBank may, in some cases, be one indicator of the potential usefulness of that sequence as a probe, the randomized sequences with a lower number of matches may also be useful as probes for DNA fingerprinting.

Calculation of the total number of different probes that can be produced from the 15-nucleotide sequence GGTGGNGATGGCTNG of the present invention comprising the characters ACGGGGGGGGTTTnn if each n is replaced with one of the four DNA bases is shown as follows. The formula $15!/(w!x!y!z!)$ calculates the permutations that can be made from a collection of bases where w is the number of A bases, x is the number of C bases, y is the number of G bases, and z the number of T bases. The number at the right of each row shown below is the calculated number of permutations of the given bases. The grand total at the bottom is the calculated total number of permutations given all combinations of substitutions for the unspecified bases. Fifteen factorial (15!) is $15 \times 14 \times 13 \times 12 \times \ldots \times 3 \times 2 \times 1$ and is equal to $1.3^{12}$, or 1.3 trillion. In probability theory, combinations are all possible arrangements, some of which may be identical. Permutations are the unique arrangements.

| n1 | n2 | A | C | G | T | $15!/(w!x!y!z!)$ |
|----|----|---|---|---|---|------------------|
| A  | A  | 3 | 1 | 8 | 3 | 900,900          |

-continued

| n1 | n2 | A | C | G | T | 15!/(w!x!y!z!) |
|----|----|---|---|---|---|----------------|
| A  | C  | 2 | 2 | 8 | 3 | 1,351,350 |
| A  | G  | 2 | 1 | 9 | 3 | 300,300 |
| A  | T  | 2 | 1 | 8 | 4 | 675,675 |
| C  | A  | 2 | 2 | 8 | 3 | 1,351,350 |
| C  | C  | 1 | 3 | 8 | 3 | 900,900 |
| C  | G  | 1 | 2 | 9 | 3 | 300,300 |
| C  | T  | 1 | 2 | 8 | 4 | 675,675 |
| G  | A  | 2 | 1 | 9 | 3 | 300,300 |
| G  | C  | 1 | 2 | 9 | 3 | 300,300 |
| G  | G  | 1 | 1 | 10| 3 | 60,060 |
| G  | T  | 1 | 1 | 9 | 4 | 150,150 |
| T  | A  | 2 | 1 | 8 | 4 | 675,675 |
| T  | C  | 1 | 2 | 8 | 4 | 675,675 |
| T  | G  | 1 | 1 | 9 | 4 | 150,150 |
| T  | T  | 1 | 1 | 8 | 5 | 270,270 |
|    |    |   |   |   |   | 9,039,030 |

The following algorithm implemented by a computer program produces random sequences by sampling without replacement:

(1) Create a master sequence containing 1 A, 1 C, 8 G's, 3 T's, and 2 N's. The master sequence contains 15 characters. Since the characters are sampled at random, the order of characters in the master sequence is not significant. If the algorithm is repeated on a randomized sequence, another random sequence will be produced. A small probability exists that this algorithm will produce a random sequence that is identical to the starting master sequence;

(2) Set i to 15, the length of the master sequence;

(3) Select a number, r, at random such that r is no less than 1 and no greater than i;

(4) Remove the character at position r from the master sequence. This is the sampling step. Since nothing is added to the master sequence, the sampling is without replacement;

(5) Add the character to the end of the new, random sequence. The master sequence now contains i-1 characters, and the new sequence 16-i; and (6) Subtract 1 from i. If i is greater than zero, proceed to step 3.

(7) The master sequence is empty, and the new sequence contains a randomized version of the master sequence.

EXAMPLE 2

Synthesis and Labeling of DNA Probes

A. Synthesis of DNA probes

The DNA probes of the present invention, each comprising a 15-nucleotide sequence according to Example 1 wherein at least one strand contains 8 G's, 3 T's, 1 C, 1 A and 2 N's (where N is A, C, G or T), were synthesized as follows.

The single-stranded DNA oligonucleotide fragments may be used as a probe. Each probe may be chemically synthesized, for example, by using an ABS 380A DNA synthesizer (Applied Biosystems, Inc., 850 Lincoln Centre Drive, Foster City, Calif. 94404) or a Systec 1450A DNA Synthesizer (Systec, Inc., 3816 Chandler Drive. Minneapolis, Minn. 55401). Many DNA synthesizing instruments are known in the art and can be used to make the single-stranded fragments. In addition, single-stranded fragments can also be conventionally prepared in substantial accordance with the procedures of Itakura et al., 1977, Science, 198:1056 and Crea et al., 1978, Proc. Natl. Acad. Sci. USA, 75:5765.

B. Labeling of DNA Probes

Two $\mu$l (~100 ng/$\mu$l) of a DNA probe synthesized as in part A of this Example was mixed with 10 $\mu$l of 10 X Kinase Buffer (600 mM Tris-HCl, pH 7.8; 100 mM MgCl$_2$; 50 mM DTT; 1 mM EDTA), 10 $\mu$l of $^{32}$P-$\gamma$-labeled ATP (available from New England Nuclear as catalog no. NEG002A), 3 $\mu$l of T4 polynucleotide kinase (available from New England Biolabs as catalog no. 201), and 75 $\mu$l of dH$_2$O. The 100 $\mu$l reaction mixture was incubated at 37° C. for 30 minutes. Labeling (% incorporation) was monitored with PEI (polyethylenimine) chromatography strips, such as Baker-Flex strips available from J. T. Baker, Inc., Phillipsburg, N.Y., 08865.

EXAMPLE 3

DNA Preparation and Analysis of RFLPs of HVRs in Genomic DNA

A. Preparation of DNA

DNA was prepared in substantial accordance with the method of Madisen et al., 1987, Am. J. Med. Genet. 27:379-390. Whole blood was collected in EDTA-containing Vacutainer (purple-stoppered) tubes. The anticoagulated whole blood is mixed with 5 volumes of warm (37° C.) Tris:ammonium chloride (0.155 M NH$_4$Cl:0.17 M Tris, pH 7.65, 9:1) in a 50-ml disposable plastic centrifuge tube and held at 37° C. for 5 minutes to lyse erythrocytes. The mixture is centrifuged at 2,000 rpm for 10 minutes to pellet nucleated cells. All but 4-5 ml of the supernatant solution is removed from the white cells in the loose reddish pellet. Ten milliliters 0.15 M NaCl is added to the pellet, which is resuspended and again centrifuged at 2,000 rpm for 10 minutes. This time the overlying fluid is carefully and entirely removed by aspiration.

The pellet consisting of nucleated cells is washed again in 0.15 M saline. Alternatively, a single wash of 25-30 ml saline may be used. The cells are pelleted and resuspended uniformly in 1 ml of high TE buffer (100 mM Tris:40 mM EDTA, pH 8.0) per 10 ml of whole blood. The cells are lysed immediately by forceful injection of 1 ml of lysis mixture (0.2% SDS; 1 M NaCl; 40 mM EDTA; 100 mM Tris, pH 8.0) per 10 ml of whole blood with a 5 ml syringe fitted with a 16- or 18-gauge needle or with an automatic pipetting device. The injection of the lysis mixture should mix the suspension sufficiently for complete and instantaneous lysis. The lysate at this stage can be stored in the cold or shipped by mail; it is stable for at least 5-6 years.

An equal volume of 1×TE-saturated phenol and chloroform (1:1:1) is added to the lysate. Mixing is continued for 30 minutes (rotary mixer) or longer (up to several hours). The organic and aqueous phases are separated by centrifugation at 2,000 rpm for 5 minutes. The upper (aqueous) phase is removed with a large-bore glass pipette. The white interphase should be mixed with high TE buffer and reextracted with phenol-chloroform. The aqueous layers are pooled and reextracted with TE-saturated phenol. The pooled aqueous layer is extracted with chloroform:isoamyl alcohol (24:1). The aqueous layer above the chloroform is saved after separation at 2,000 rpm for 5 minutes.

One-tenth volume of 4 M ammonium acetate is added to the aqueous layer from the previous step, and the solution is mixed well. A volume of isopropanol equal to that of the mixture is added, and the tube is mixed by inversion and swirling. The long strands of DNA are fished from the solution with the curved end of a pasteur pipette, washed with 70% ethanol, air-dried, and redissolved in low TE buffer (1 ml per 7-10 ml of original blood) on a rotator at 4° C. Alternatively, if small amounts of DNA are extracted by this method, it may be necessary to centrifuge for 10 minutes at 10,000 rpm to collect the nucleic acids.

The preparations are stored at 4° C. or −70° C. in Cryotubes. For prolonged storage, 5 μl of chloroform is added to each ml of DNA solution and mixed prior to sealing the tube.

B. Analysis of RFLPs

1. Digestion of DNA 10-100 μl (~5 μg) of genomic DNA prepared as described in part A above are added to 10 μl of 10×HaeIII buffer (Buffer M from Boehringer Mannheim) and water to 100 μl of $H_2O$. Five μl (~8-12 units/μl) of restriction enzyme HaeIII (Boehringer Mannheim) are added to the DNA solution, and the resulting reaction is incubated at 37° C. for 2 hours.

2. Electrophoresis of Digested DNA

The HaeIII-digested DNA is loaded onto a 0.8% agarose gel (0.8 g agarose per 100 ml 1×Electrophoresis Buffer (Maniatis et al., 1982, Molecular Cloning - A Laboratory Manual, p. 156, Cold Spring Harbor Laboratory. N.Y.) and electrophoresed overnight at 60 V, 45 mA. Visualization of the electrophoresed DNA is accomplished by staining the gel in a dilute solution of ethidum bromide (~3.0 μg/ml) for 30 minutes. The gel is placed in Denaturing Solution (0.5 N NaOH; 0.15 M NaCl) for 30 minutes at room temperature and then in Neutralization Solution (0.5 M Tris-HCl, pH 8.0; 0.15 M NaCl) for 30 minutes at room temperature. The gel is then placed on two pieces of Whatman 3 MM paper moistened with Neutralizing Solution and placed in gel dryer at 42° C. until almost dry. The gel should be slightly moist without a cloudy background. A full-size (22 cm) gel, for example, is dried for 45 minutes. The slightly moist gel is then wrapped in a plastic wrap, such as Saran wrap, and placed between 2 glass plates.

3. Hybridization

A small amount (~10 ml) of Hybridization Solution (100 ml of Hybridation Solution contains: 30 ml of 20×SSC (0.3 M sodium citrate; 3 M NaCl); 40 ml of formamide; 1 ml of Bailey's or O'Darby's Irish Cream Liquor (Elbrecht et al., 1987, BMBiochemica 4: 12-13); 5 ml of 0.1 M EDTA, pH 8.0 and 24 ml of $dH_2O$) is used to release the dried gel from the paper backing. The Hybridization Solution may be stored at room temperature for one week.

The labeled probe, prepared in substantial accordance with the procedure of Example 2, is added to ~10 ml of Hybridization Solution. No prehybridization is necessary. The dried gel is placed in a plastic bag; the probe mixture is added, and the bag is sealed. Hybridization is carried out for 3 hours, or overnight, at room temperature. After this incubation, the hybridization solution is poured off and the gel is washed for 1 hour at room temperature first with 2×SSC, then with 1×SSC. If it is necessary to remove background, these two washes may be followed by two washes with 0.8×SSC, first for 1 hour at room temperature and then for 1 hour at 37° C.

The HaeIII digested DNA fragments hybridizing with a DNA probe according to the present invention are detected by exposing the washed gel to a Kodak X-ray film with an intensifier screen for an appropriate period of time to detect hybridizing fragments (typically, 3 hours to overnight). The resulting RFLPs observed produce an individual specific DNA fingerprint, enabling identification of differences between even closely related individuals. In addition to direct blotting as described above, it is also possible to obtain DNA fingerprints by conventional methods of Southern blotting.

EXAMPLE 4

Twin Zygosity Determination

The zygosity of sets of twins was determined by analysis of their DNA using the DNA probe GGTGGAGATGGCTGG as described in Example 2 as follows. DNA was isolated from each blood sample in substantial accordance with the procedure of Example 3. The labeled probe was prepared in substantial accordance with the procedure of Example 2. Approximately 5 μg of each DNA sample was digested with restriction enzyme HaeIII for 2 hours at 37° C. The HaeIII-digested DNA samples were electrophoresed overnight through a 0.8% agarose gel. The gel was dried, and the probe was hybridized with the gel, all in substantial accordance with the procedure of Example 3. An example of the results obtained is shown in FIG. 1.

Using the synthetic DNA probe GGTGGAGATGGCTGG, the zygosity of more than 73 sets of twins has been determined to date. The results of the DNA analysis of 52 sets of twins that were initially analyzed are shown in Table I. An example of the patterns obtained is shown in FIG. 1.

TABLE I

| | Twin Zygosity Determinations | | |
|---|---|---|---|
| CASE | AGE[a] (in years) | SEXES | DNA PATTERN |
| 0001 (VA-4149/50) | A | MM | Nonidentical |
| 0002 (VA-5001/02) | A | MM | Identical |
| 0003 (VA-5015/16) | A | MM | Identical |
| 0004 (VA-5027/28) | A | MM | Nonidentical |
| 0005 (VA-5051/52) | A | MM | Identical |
| 0006 (VA-5053/54) | A | MM | Nonidentical |
| 0007 (VA-5055/56) | A | MM | Nonidentical |
| 0008 (VA-5065/66) | A | MM | Nonidentical |
| 0009 (VA-5087/88) | A | MM | Identical |
| 0010 (VA-5091/92) | A | MM | Identical |
| 0011 (VA-5145/46) | A | MM | Identical |
| 0012 (VA-5153/54) | A | MM | Identical |
| 0013 (VA-5157/58) | A | MM | Nonidentical |
| 0014 (VA-5185/86) | A | MM | Nonidentical |
| 0015 (VA-5191/92) | A | MM | Nonidentical |
| 0016 (VA-5195/96) | A | MM | Nonidentical |
| 0017 (VA-5209/10) | A | MM | Nonidentical |
| 0018 (VA-5223/24) | A | MM | Nonidentical |
| 0019 (VA-5227/28) | A | MM | Identical |
| 0020 (VA-5235/36) | A | MM | Nonidentical |
| 0021 (VA-5259/60) | A | MM | Nonidentical |
| 0022 (88-5082/83) | 65 | FF | Identical |
| 0023 (88-5087/88) | 64 | FF | Nonidentical |
| 0024 (88-5089/90) | 66 | FF | Nonidentical |
| 0025 (88-5120/21) | 36 | FF | Identical |
| 0026 (88-5122/23) | 11 | FF | Nonidentical |
| 0027 (88-5124/25) | <1 | MM | Identical |
| 0028 (88-5126/27) | 2 | FF | Identical |
| 0029 (88-5128/29) | 2 | MM | Identical |
| 0030 (88-5144/45) | 1 | FF | Identical |

TABLE I-continued

Twin Zygosity Determinations

| CASE | AGE[a] (in years) | SEXES | DNA PATTERN |
|---|---|---|---|
| 0031 (88-5146/47) | 30 | FF | Nonidentical |
| 0032 (88-5148/49) | 27 | FF | Identical |
| 0033 (88-5003/04) | 1 | MM | Nonidentical |
| 0034 (88-5005/06) | 2 | MM | Nonidentical |
| 0035 (88-BM-23B/43A) | 19 | FF | Identical |
| 0036 (88-5024/25) | 0.25 | MM | Identical |
| 0037 (88-5030/31) | 6 | MM | Nonidentical |
| 0038 (88-5041/42) | 7 | FF | Nonidentical |
| 0039 (88-5054/55) | 35 | FF | Nonidentical |
| 0040 (88-5062/63) | 11 | MM | Nonidentical |
| 0041 (88-5096/97) | 9 | MM | Nonidentical |
| 0042 (88-5112/13) | 0.5 | FF | Identical |
| 0043 (88-5114/15) | 9 | FF | Nonidentical |
| 0044 (88-5150/51) | 6 | FF | Nonidentical |
| 0045 (88-5155/56) | 34 | FF | Nonidentical |
| 0046 (88-5157/58) | 58 | FF | Nonidentical |
| 0047 (88-5159/60) | 0.92 | MM | Nonidentical |
| 0048 (88-5182/83) | 56 | FF | Identical |
| 0049 (88-5200/01) | 6 | FF | Nonidentical |
| 0050 (89-M-0001/02) | 1 | MM | Identical |
| 0051 (89-M-0003/04) | 6 | MM | Nonidentical |
| 0052 (89-M-0012/13) | 19 | MM | Identical |

[a] A is adult of unknown age.

Cases 0001–0021 shown in Table I were tested by one or more of the following methods: finger prints, appearance, twins verification, and blood type. In cases 0001–0020, results from the other methods agreed with and confirmed the DNA analysis. Only in case 0021 were the results from DNA analysis different from the results obtained by other methods. This may be due to the fact that one of the twins had been multiply-transfused and was on chemotherapy treatment for cancer at the time the sample was taken.

The results of the gel analyses of the following cases from Table I are shown in FIG. 1: 0001 - lanes 9 and 10; 0002 - lanes 11 and 12; 0003 - lanes 13 and 14; 0004 - lanes 3 and 4; 0005 - lanes 15 and 16; 0006 - lanes 5 and 6; 0009 - lanes 17 and 18; 0014 - lanes 7 and 8.

Thus, DNA analysis, using a DNA probe according to the present invention, may be used to detect RFLPs of HVRs, as illustrated in Table I. The results in Table I showed that 31 sets of twins exhibited different band patterns and therefore were dizygotic, whereas 21 sets of twins exhibited identical band patterns, and were therefore monozygotic.

EXAMPLE 5

Determination of Cell Chimerism After Bone Marrow Transplantation

The DNA probe GGTGGAGATGGCTGG as described in Example 2 was used to identify the donor or recipient origin of hematopoietic cells after allogenic bone marrow transplantation. Using this synthetic DNA probe, more than 73 different bone marrow samples have been analyzed to date. The DNA for analysis was prepared from each bone marrow sample as follows. Small pieces of bone marrow were mixed with 1.0 ml of Phosphate Buffered Saline (1 liter of PBS contains 80 g NaCl, 2 g KCl, 11.5 g NaHPO$_4$ and 2 g KH$_2$PO$_4$) and 1.0 ml of Lysis Buffer (Lysis Buffer is 0.2% SDS; 1 M NaCl; 40 mM EDTA; 100 mM Tris-HCl, pH 8.0). The mixture was vortexed, and 200 μl of a Proteinase K solution (Boehringer Mannheim; the solution is 100 mg of Proteinase K in 10 ml of 20 mM Tris-HCl, pH 8.5) were added. This mixture was incubated at 37° C. for 1 hour with shaking to yield a cell lysate. DNA for analysis was also prepared from peripheral blood as described in Example 3A.

An equal volume of 1×TE-saturated phenol and chloroform (1:1:1) was added to the lysate. Mixing was continued on a wrist-action shaker for 30 minutes or longer, up to several hours. The organic and aqueous phases are separated by centrifugation at 2,000 rpm in a Beckman J-6 centrifuge for 5 minutes. The upper (aqueous) phase was removed with a large-bore pipette. The white interphase was sometimes mixed with TE buffer and reextracted with phenol. The aqueous layers were pooled and reextracted with TE-saturated phenol and chloroform. The pooled aqueous layer was extracted with chloroform and isoamyl alcohol, 24:1. The aqueous layer above the chloroform was saved after separation at 2,000 rpm for 5 minutes.

One-tenth volume of 4 M ammonium acetate was added to the aqueous layer obtained after the extractions as described above, and the solution gently mixed. Then, 1.5 volumes of cold isopropanol were added to each tube, and the tube was mixed by inversion and swirling. The long strands of DNA were fished from the solution with the curved end of a pasteur pipette (or alternatively, the solution was centrifuged at 2,000–10,000 rpm to collect the DNA), washed with 70% ethanol, air-dried, and the DNA redissolved in TE buffer.

The bone marrow-derived or peripheral blood-derived DNA thus obtained was digested with restriction enzyme HaeIII (alternatively, AluI, HinfI, MboI or SauC13AI may be used) in substantial accordance with the procedure of Example 3B. Analysis of the restriction fragment length polymorphisms with the DNA probe GGTGGAGATGGCTGG was done in substantial accordance with the procedure of Example 3. The results from 46 different bone marrow samples initially analyzed are shown in Table 2. An example of the patterns obtained from 5 sets of bone marrow donors and recipients is shown in FIG. 2.

TABLE II

Bone Marrow Transplantation-DNA Analysis

| Test No. | | Day Post-Transplant[d] | D/R Sex | Pattern (D) | (R) | (D + R) |
|---|---|---|---|---|---|---|
| 1 | (23/24-BM-87) | 33 | M/M | + | − | − |
| 2 | (20/21-BM-87) | nd | M/M | − | + | − |
| 3 | (10-BM-88) | nd | F/F | + | − | − |
| 4[a] | (12-BM-88) | 33 | F/F | + | + | + |
| 5 | (16-BM-88) | 141 | M/M | − | + | − |
| 6 | (20-BM-88) | 90 | M/M | − | + | − |
| 7 | (13-BM-88) | 22 | M/M | + | + | + |
| 8 | (26-BM-88) | 28 | F/M | − | + | − |
| 9 | (30-BM-88) | 90 | M/M | + | − | − |
| 10 | (31-BM-88) | 180 | F/F | + | − | − |
| 11 | (33-BM-88) | 90 | F/M | + | − | − |
| 12 | (37-BM-88) | nd | M/M | − | + | − |
| 13[a] | (32-BM-88) | 90 | F/F | + | + | + |
| 14[b] | (41-BM-88A) | nd | M/M | − | + | − |
| 15 | (42-BM-88) | 142 | M/M | + | − | − |
| 16 | (44-BM-88) | 60 | M/M | + | − | − |
| 17 | (42c-BM-88) | 189 | M/M | + | − | − |
| 18 | (47-BM-88) | 274 | M/M | − | + | − |
| 19 | (50-BM-88) | 28 | F/F | + | − | − |
| 20 | (48-BM-88B) | 26 | M/M | + | − | − |
| 21 | (33-C-BM-88) | 180 | F/M | + | − | − |
| 22 | (88-BM-45D) | nd | F/M | + | − | − |
| 23 | (88-BM-38-B) | nd | M/M | + | − | − |
| 24[c] | (88-BM-62) | nd | #M | + | − | − |
| 25 | (88-BM-50C) | 103 | F/F | + | − | − |
| 26[c] | (88-BM-64) | 52 | #M | + | − | − |
| 27 | (88-BM-72) | 15 | F/M | + | − | − |

TABLE II-continued
Bone Marrow Transplantation-DNA Analysis

| Test No. | | Day Post-Transplant[d] | D/R Sex | Pattern (D) | (R) | (D + R) |
|---|---|---|---|---|---|---|
| 28 | (88-BM-67) | 346 | M/M | − | + | − |
| 29 | (88-BM-66) | 255 | F/M | + | − | − |
| 30[c] | (88-BM-69) | 72 | #M | + | + | + |
| 31 | (88-BM-77) | 30 | F/M | + | − | − |
| 32 | (88-BM-76) | 28 | F/M | + | − | − |
| 33 | (88-BM-081) | 180 | M/M | + | − | − |
| 34 | (88-BM-085) | 28 | M/M | + | − | − |
| 35 | (88-BM-083) | nd | -M | + | + | + |
| 36 | (88-BM-080) | 28 | F/F | + | − | − |
| 37[a] | (88-BM-087) | 360 | F/F | − | + | − |
| 38[a] | (88-BM-006) | 381 | F/F | − | + | − |
| 39 | (89-BM-005) | 180 | F/F | + | + | + |
| 40 | (89-BM-004) | 180 | F/M | + | − | − |
| 41 | (89-BM-003) | nd | -M | + | − | − |
| 42 | (89-BM-011) | nd | -M | + | − | − |
| 43 | (89-BM-012) | 75 | M/M | + | − | − |
| 44 | (89-BM-016) | 90 | F/F | + | − | − |
| 45 | (89-BM-019) | nd | M/M | + | − | − |
| 46 | (89-BM-022) | nd | M/M | + | − | − |

[a]Test Nos. 4, 13, 37 and 38 are all from same patient; mixture of donor and recipient cells detected at 33 and 90 days post transplant, followed by relapse (no donor cells detected after 360 days post transplant).
[b]Sample from tumor, not from blood.
[c]Test nos. 24, 26 and 30 are all from same patient.
[d]nd is not determined.

Those samples (30 of the 46 samples shown in Table II) exhibiting RFLP patterns of the donor type only indicated engraftment of donor cells in the bone marrow tissue examined. Those samples (10 of the 46 samples shown in Table II) exhibiting RFLP patterns of recipient type only indicated lack of engraftment of donor cells at the time of sampling. Those samples (6 of the 46 samples shown in Table II) exhibiting mixed donor- and recipient- type RFLP patterns indicated mixed chimerism. In one case (test no. 44) mixed chimerism was not detected 90 days post-transplant by DNA analysis, but the patient later relapsed. In general, when mixed chimerism was detected by DNA analysis, the patient later relapsed. Samples of bone marrow or peripheral blood were obtained from patients at various times following transplantation to study the engraftment process. When the transplant procedure appeared clinically to be successful, DNA from patients studied at intervals of 1-2 months post-transplant consistently exhibited only donor type patterns without any trace of recipient-derived patterns. Those patients with failed grafts showed a DNA pattern of recipient type.

We claim:

1. A DNA probe which is selected from the group consisting of

| | |
|---|---|
| GGTGGAGATGGCTGG, | GGCGTGAGGGAGGTT, |
| AATGCGGTGGGGGGT, | GGGCATAGGTTGGGG, |
| ATCGTGGTGGAGGGG, | GGGCTTTGAGGGGGA, |
| ATTGGGCGGGGAGTG, | GGGGCAGTAGTGGGT, |
| CAGTGGTGTGGAGGG, | GGGGGGAGTTGCAGT, |
| CGGAGGAGTTGTGGG, | GGGGGGTGCTGGAAT, |
| CGGGGGATGTTGGGA, | GGGGTATGTGCGAGG, |
| CGGGGTGGGGTAATG, | GGTGGGCTTGAGGGA, |
| CGGGGTGTGAGGTAG, | GTAAGGGGGGCTTGG, |
| CGGTTGTGAGGGGGA, | GTGAGGCGGGTGAGT, |
| CTGGTGTGGAGGAGG, | GTGCAGGATGGTGGG, |
| GAATGGGGCGGTGTG, | GTGGTATGGGAGCGG, |
| GACGGTGGTGAGGTG, | GTGTGGGTGGCAGAG, |
| GAGTACGGTGGGGTG, | TAAGGTGGGGGCGGT, |
| GAGTCGGTGGGTAGG, | TAGCGGATGGGGTGG, |
| GAGTGGGTTAGGGGC, | TGAGAGTGGGGGGCT, |
| GGCGGGTGGTGGTAA, | TGGGAGTGCGAGGGT, |
| GGCGGTTTAGGAGGG, | TGGGGGGAATTCGGG, |

2. A DNA probe according to claim 1 comprising a 15-nucleotide sequence GGTGGAGATGGCTGG.

3. A DNA probe according to claim 1 comprising a 15-nucleotide sequence CTGGTGTGGAGGAGG.

* * * * *

UNITED STATES PATENT AND TRADEMARK OFFICE
CERTIFICATE OF CORRECTION

PATENT NO.    :    5,097,024

DATED         :    March 17, 1992

INVENTOR(S)   :    Hodes, et al.

It is certifed that an error apears in the above-identified patent and that said Letters Patent is hereby corrected as shown below:

At Column 5, line 24 of the patent, the DNA sequence "GGGGTGGGG" is indicated. This sequence should read -- GGG_ _GTGGGG --.

At Column 5, line 25 of the patent, the DNA sequence "GTGGG" is indicated. This sequence should read -- G_ _ _ _TGGG --.

At Column 7, line 13 of the specification, between the words "sequence" and "a" insert a hyphen, -- - ---.

At Column 11, lines 1-5, the patent reads:

"M13 Tandem     M13 Tandem
§------1------ §------2------
M13: GAGGGTGGNGGNTCTGAGGGTGGNGGNTCT"

These lines should aligned to read in the following manner:
--
    M13 Tandem       M13 Tandem
    §------1------¶§------2------¶
M13: GAGGGTGGNGGNTCTGAGGGTGGNGGNTCT

--.

UNITED STATES PATENT AND TRADEMARK OFFICE
CERTIFICATE OF CORRECTION

PATENT NO.    :    5,097,024

DATED         :    March 17, 1992

INVENTOR(S)   :    Hodes, et al.

It is certifed that an error apears in the above-identified patent and that said Letters Patent is hereby corrected as shown below:

In Claim 1, Column 20, line 32 of the specification, the patent reads "TGGGGGGAATTCGGG,". The patent should read:
-- TGGGGGGAATTCGGG. --.

Signed and Sealed this

Fifteenth Day of June, 1993

Attest:

MICHAEL K. KIRK

*Attesting Officer*    *Acting Commissioner of Patents and Trademarks*